United States Patent [19]

Bondi et al.

[11] Patent Number: 4,756,710
[45] Date of Patent: Jul. 12, 1988

[54] PH-MEDIATED DRUG DELIVERY SYSTEM

[75] Inventors: Joseph V. Bondi, Collegeville; Alice E. Loper, Lederach, both of Pa.; Edward M. Cohen, Princeton Junction, N.J.

[73] Assignee: Merck & Co., Inc., Rahway, N.J.

[21] Appl. No.: 835,585

[22] Filed: Mar. 7, 1986

Related U.S. Application Data

[63] Continuation-in-part of Ser. No. 720,652, Apr. 4, 1985.

[51] Int. Cl.$^4$ .............................................. A61K 9/00
[52] U.S. Cl. .................................... 424/449; 424/434
[58] Field of Search ............... 604/890, 891, 896, 897, 604/892, 289, 290, 304, 307, 308; 128/130; 424/14, 21, 22, 24, 28, 400, 422, 424, 425, 434

[56] References Cited

U.S. PATENT DOCUMENTS

| | | | |
|---|---|---|---|
| 3,797,494 | 3/1974 | Zaffaroni | 604/897 |
| 4,303,637 | 12/1981 | Shell et al. | 424/22 |
| 4,440,777 | 4/1984 | Zupan | 424/45 |
| 4,460,368 | 7/1984 | Allison et al. | 604/896 |
| 4,484,921 | 11/1984 | Swanson et al. | 604/892 |
| 4,568,343 | 2/1986 | Leeper et al. | 424/28 |
| 4,645,502 | 2/1987 | Gale et al. | 604/896 |

FOREIGN PATENT DOCUMENTS

| | | | |
|---|---|---|---|
| 0159168 | 10/1985 | European Pat. Off. | 424/28 |
| 3319469 | 11/1984 | Fed. Rep. of Germany | 424/28 |
| 2093344 | 9/1982 | United Kingdom | 424/28 |
| 2158355 | 11/1985 | United Kingdom | 424/22 |

OTHER PUBLICATIONS

*The Merk Index*, 10th Ed., Merk & Co., Rahway, N.J., Composition No. 7740, 8863 and 9284.

Primary Examiner—Dalton L. Truluck
Assistant Examiner—Mark F. Colosimo
Attorney, Agent, or Firm—Alice O. Robertson; Michael C. Sudol

[57] ABSTRACT

A method and device for delivering acidic or basic drugs in a controlled delivery system is described.

9 Claims, 1 Drawing Sheet

PH-MEDIATED DRUG DELIVERY SYSTEM

This is a continuation-in-part of application Ser. No. 720,652, filed Apr. 4, 1985.

BACKGROUND OF THE INVENTION

Sustained release devices for controlled transdermal delivery of drugs is a highly useful method of supplying medication when it is beneficial to administer medication continuously and at a relatively low rate. Sustained release devices include transdermal or transmucosal patches or bandages, implants, osmotic devices and the like. Transdermal patches and bandages are especially desirable as a means for avoiding the uncertainties of oral administration and the inconvenience of administration by injection.

STATEMENT OF THE INVENTION

According to the present invention it has been discovered that by controlling the pH in the drug reservoir of transdermal or transmucosal delivery devices, a drug delivery system is provided in which the unionized form of a weakly acidic or basic drug can be delivered at a desired constant rate. It has further been discovered that by controlling the pH in the drug reservoir a transdermal drug delivery system can be provided whereby the unionized form of the drug can be delivered to the skin at a rate which is known to cause little or no irritation to the skin. The invention is also directed to a method for controlled release of a weakly acidic or basic drug which comprises providing the drug in a pH controlled reservoir, said reservoir comprising a buffered solution of the drug and allowing the drug to pass from the drug reservoir through a membrane selectively permeable to the unionized form of the drug and substantially impermeable to the ionized form of the drug. One of the preferred embodiments of the present invention is a method for administering timolol transdermally and a delivery system therefor. The expression "transdermal" is meant to include "transmucosal". Thus, "transdermal delivery systems" and "transdermal delivery devices" are intended to include transmucosal delivery systems and transmucosal delivery devices.

DETAILED DESCRIPTION OF THE INVENTION

By providing the drug in a pH controlled reservoir which is separated from the dermal surface by a membrane permeable to the unionized absorbable form of the drug but substantially impermeable to the ionized difficulty absorbable form and other materials, positive control of the rate of delivery may be achieved.

The steady state rate of flow of the drug or flux from the reservoir or donor phase across a membrane into a receptor phase where the concentration of the drug is insignificant or substantially zero is seen in the following relationship $$J = (K.D.C)/h \qquad (1)$$

where J is the flux, K is the partition coefficient between the drug reservoir and the membrane, D is the drug diffusion coefficient in the membrane, C is the concentration of the unionized drug in solution in the reservoir and h is the membrane thickness.

In any particular system, when the steady state line describing the amount of drug transported through a membrane versus time is extrapolated to the time axis, the intercept is described by the relationship $$T = h/6D \qquad (2)$$

where T is the time lag. Thus, after determining T, D may be calculated. By experimentally determining flux, and substituting in equation (1), K may be obtained. Having thus determined K and D, the desired flux may be achieved by making appropriate modifications of the pH, thereby the concentration, and/or the thickness of the membrane. The appropriate modifications in pH may be arrived at by preparing a series of buffer solutions containing a known quantity of the salt form of drug at various pH values and substituting in the Henderson-Hasselbalch equation, $$pH = pk_a - \log \frac{[\text{unionized form}]}{[\text{ionized form}]} \qquad (3)$$

C, the concentration of the unionized form, may be calculated.

The modification in pH may be accomplished with the selection of appropriate buffering agents. Phosphates and carbonate buffer systems appear to be the most suitable although tris(hydroxymethyl)aminomethane and boric acid/borate buffer systems also may be employed. However, as subsequently will be shown, the solubility of the drug in the particular liquid vehicle or medium is also critical since if the buffer system decreases the solubility in the particular medium, the flux will be decreased even though the pH may appear to be appropriate for a high flux value.

While the reservoir vehicle, i.e., the solvent for the drug, necessarily is of a substance in which both the drug and the salt of the drug is soluble, it is not limited to water. In fact, an aqueous system would be rather limiting from a practical standpoint. In addition to bulk and awkwardness of providing for a transdermal patch employing a highly mobile liquid, an aqueous system would require preservatives and possibly sterilization to prevent microbial growth. More suitable reservoir vehicles are certain polyhydroxy compounds or partially aqueous preparations possessing self-sterilizing properties. Such vehicles include sorbitol solution U.S.P., propylene glycol, glycerol, and the like. Moreover, certain solids and semisolid materials also will provide suitable media to effect positive pH control.

The preferred materials for the reservoir vehicle are hydrogels, i.e., polymeric materials which swell in water and retain a significant amount of water in its structure but which will not dissolve in water. The property of hydrogels permitting small molecules to diffuse therethrough is advantageous as a medium for bearing a buffer solution containing drug. Hydrogels may be prepared in the form of gels, films and porous sponges. Hydrogel polymers include poly(hydroxyalkyl methacrylate)s of which poly(2-hydroxyethyl methacrylate), poly(glyceryl methacrylate) and poly(hydroxypropyl methacrylate) are well-known and identified in the literature as (P-HEMA), (P-GMA) and (P-HPMA), respectively. Other hydrogel polymers include poly(acrylamide), poly(methacrylamide), poly(N-vinyl-2-pyrrolidine), and poly(vinyl alcohol).

For the proper operation of the present invention, it is critical and essential that the membrane selected be one through which only the unionized form of the drug can diffuse and further that it be impermeable to the ionizable form of the drug and to other reservoir components. Moreover, inasmuch as the magnitude of the flux is provided by the concentration of the diffusing drug species, the membrane selected should be one which has negligible rate controlling effect on the drug.

One useful application of the present invention is the provision of the drug from a pH controlled reservoir in a transdermal delivery system in the form of a patch or bandage. By the expression "transdermal delivery system" as herein employed is meant to include backing member, a drug reservoir and a selectively permeable membrane. By "transdermal patch" or "transdermal bandage" is meant the transdermal delivery system plus a means to attach the system to the skin. The attachment means may be a tape which fits over the system or preferably a layer of adhesive coating as subsequently more fully described.

The transdermal delivery systems comprises a backing member, a drug reservoir and a selectively permeable membrane. The term "reservoir" as used herein refers to the entire drug containing portion of the bandage and embraces a broad class of structures which is able to perform the intended function. It refers to drug containing semisolid matrixes (reservoir vehicle) with or without containers or to porous or microporous structures as hereinafter described. The drug reservoir contains the buffered solution of the drug. The medium for the reservoir may be liquid, semi-solid or solid as previously stated. Whatever the medium, it is essential that there is free mobility of the ionized and unionized drug and of the buffering agent. Although a liquid system may be most desirable from the standpoint of free mobility of the solutes, it is less convenient in actual use. A semi-solid material such as a gel is therefore more suitable. Solid films in which buffered solutions of drug may migrate or solid open foam matrixes in which buffered liquid solutions of drugs may migrate are also within the contemplation of the present invention.

The amount of drug incorporated in the drug delivery device varies depending on the particular drug, the therapeutic effect and the period of time over which it is to be accomplished. It will also depend on the activity of the drug. The amount readily may be determined from the known activity of the drug and preliminary in vitro diffusion studies with the membrane selected.

The selectively permeable membrane, as previously stated, must be a membrane which is permeable to the unionized drug but is impermeable to the ionized form of the drug and other non-drug materials. The membrane suitable for a particular drug will be dependent on the nature of the drug. However, suitability of a particular membrane for a particular buffered drug solution may be readily determined by a preliminary tests in a diffusion cell or similar testing device. Illustrative of suitable membranes may be named Celgard saturated with mineral oil, polyurethane and ethylene vinyl acetate which have been found to be useful when timolol is the drug. These membranes are also expected to be useful in drugs such as indomethacin, enalapril maleate, scopolamine hydrochloride, clonidine hydrochloride, nifedipine hydrochloride, pseudoephedrine hydrochloride, pyrilamine maleate, protryptyline hydrochloride, cyclobenzaprine hydrochloride, chlorpheniramine maleate, amitryptyline hydrochloride, fluphenazine hydrochloride and other salt forming acidic and basic drugs which find application in various therapeutic uses such as antihypertensives, tranquilizers, analgesics, antirheumatics, anticholinergics, antimigraine drugs, $\beta$-blockers, antianginal drugs and others.

The impermeable backing member 11 is preferably of a polyester occlusive film. Other materials suitable for a backing include foil, polyethylene coated foil, polyethylene, polyester, polypropylene and the like. Other backing members which have been found to be suitable in other transdermal devices may be employed in the systems of the present invention.

The attachment means may be a tape which fits over the system or a layer of adhesive coating which will adhere to the dermal surface. When it is the latter, it is necessary for the drug to diffuse freely through the adhesive. The adhesive necessary for the drug is on which will permit free passage of the drug. The transdermal delivery system and transdermal bandage can be described more fully with reference to the drawings.

Figure 1:
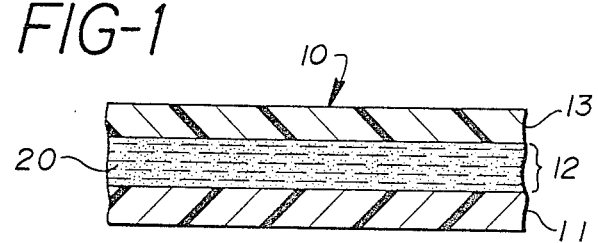
FIG. 1 is a fragmentary enlarged cross-sectional view depicting the essential component elements of a transdermal delivery system.

As illustrated in FIG. 1, the transdermal delivery system 10 comprises a backing member 11 having a drug reservoir 12 on one surface thereof. On the side of the drug reservoir opposite that facing the backing member 11, is placed a selectively permeable non-rate-controlling membrane 13. The drug reservoir contains a pH buffered solution of a drug. In the embodiment illustrated in FIG. 1, the buffered solution may be contained in a semi-solid matrix such as a gel matrix. It also may be contained in certain polymeric materials such as polyacrylate films having incorporated therein water-binding auxiliary substances such as polyethylene glycol 400, which films initially appear solid but on application to the skin operate in a manner similar to a semi-solid gel. The buffered medium must be such that there is free mobility and interchange of ions and dissolved molecules to perform the buffering function.

Figure 2:
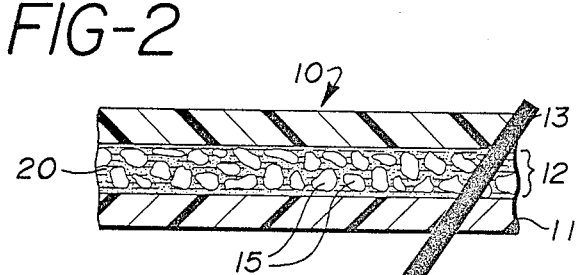
FIG. 2 is a fragmentary enlarged cross-sectional view of another embodiment of the present invention providing for a modification in the drug reservoir.

FIG. 2 illustrates an embodiment in which the buffered solution of the drug is uniformly distributed in the interstices 20 of a porous matrix material 15 shown in cross-section forming reservoir 12. The pores must be open pores permitting free movement of the buffer solution. The impermeable backing 11 and selectively permeable membrane facing 13 are positioned at opposite sides of the reservoir.

Figure 3:
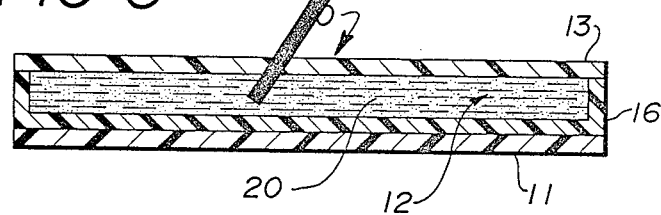
FIG. 3 is an enlarged cross-sectional view of another embodiment illustrating sill another modification in the drug reservoir.

FIG. 3 illustrates an embodiment employed when the buffered solution is liquid and therefore must be contained. The reservoir 12 then is in the form of a hollow container 16 having an interior chamber containing the drug solution. The wall or surface of the drug reservoir remote from the backing member 11 and open is covered with a selectively permeable membrane 13. This embodiment is not necessarily limited to a liquid buffered solution. A gel or a porous or microporous matrix material also may be contained in a hollow container. The hollow container may be of the same impermeable material as is the backing member. In a modification (not shown), it may be provided by a cavity or a hollowed out section of the backing material.

Figure 1A:
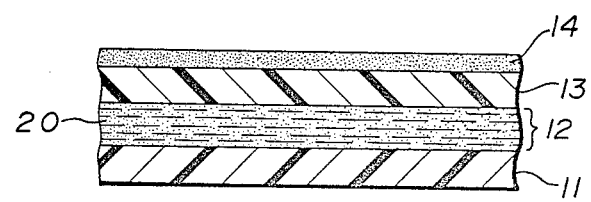
FIG. 1a is a view similar to FIG. 1 which includes an adhesive layer functioning as a means for attachment to the skin.

FIG. 1a illustrates a transdermal patch or bandage incorporating the transdermal delivery system illustrated in FIG. 1. The patch is obtained by an adhesive coating 14 along the surface of the selectively permeable membrane 13 remote from the side adjacent to the drug reservoir. This adhesive coating serves as a preferred means for attaching the transdermal device to the skin or mucosa. Its composition and thickness are such that it does not constitute a significant permeation barrier to the drug. Usually it is in the range of from about 0.01 to 7 millimeters in thickness.

Appropriate adhesives for use in the transdermal bandages depend in part on the membrane employed. Thus, if the membrane is Celgard saturated with mineral oil, the adhesive should be rubber based adhesives, or mixtures of polyisobutylene and mineral oil. If the membrane is polyurethane or ethylene vinyl acetate, acrylic adhesives are suitable. Silicone adhesives also may be useful.

The following examples illustrate the invention but are not to be construed as limiting:

EXAMPLE I

The following operation illustrates with timolol the relationship among pH, the concentration C, of the timolol base in solution in the reservoir, and the flux calculated from the data as well as the observed flux obtained by placing the compositions behind the selected membrane in a diffusion cell and measuring the rate of release into an isotonic phosphate buffer of pH 7.4.

By acrylic adhesives is meant polymers of various esters of acrylic or methacrylic acid, acrylamide, methacrylamide, N-alkoxyalkyl or N-alkyl-acrylamides. By rubber based adhesives is meant adhesives based on the various rubbers such as styrene-butadiene, polyisobutylene, polybutadiene, polyisoprene, S-I-S (polystyrene-polyisoprene-polystyrene) and S-B-S (polystyrene-polybutadiene-polystyrene) block copolymer rubbers; or on other elastomers such as polyurethane rubbers.

As a first step in determining the relationship between pH, concentration of timolol, its pK and the pH of the reservoir, an aqueous solution of 7.0 mg/ml of timolol was placed in a diffusion measuring cell fitted with a 1.5 mil (0.0038 cm) thick silicone membrane and the transport of timolol from the reservoir of the test cell to an isotonic pH 7.4 receptor phase was measured over a period of about eight hours by sampling the solution in the receptor phase, assaying this solution for drug by direct ultraviolet assay method and calculating the drug concentration over time, thereafter plotting the drug diffused per square centimeter versus time and calculating the regression line. From the readings obtained, the steady state flux, J, in the system was found to be 943.67 mcg/cm$^2$/hr and when the plot of the amount transported vs time was extrapolated to the time axis, the time lag was found to be $9.6 \times 10^{-3}$ hour.

The foregoing data was then substituted in equations (1) and (2) to obtain value for D of $2.5 \times 10^{-4}$ cm$^2$/hr and for K, the value of 2.05.

A series of aqueous buffer solutions containing 15 mg/ml of timolol maleate were then prepared and the concentration of the timolol base calculated employing the Henderson-Hasselbach equation (3) and the known pK$_a$ of 9.2 for timolol. From the calculated concentration of the timolol base, the previously determined values for D and K and the known thickness of the membrane, the steady state flux was calculated (equation (1)). Thereafter, the steady state flux was determined experimentally by measuring the transport of timolol at each pH from the buffer system into an isotonic receptor phase through the silicone membrane. The results obtained are seen in Table I and good correlation can be seen between the calculated flux and the observed flux.

TABLE I

| pH | $C_s$ Timolol Base (mg/ml) | $J_c$ Calculated Flux (mcg/cm$^2$/hr) | $J_{obs}$ Observed Flux (mcg/cm$^2$/hr) |
|---|---|---|---|
| 7.5 | 214.8 | 29 | 25 |
| 7.8 | 417.7 | 56 | 55 |
| 8.0 | 648.7 | 87 | 90 |
| 8.5 | 1816 | 244 | 223 |
| 9.0 | 4209 | 566 | 575 |

EXAMPLE II

A lipophilic microporous membrane also may be employed in the practice of the present invention by impregnating the micropores with lipophilic material. This is made possible by the difference in solubility of timolol and timolol maleate. Timolol has solubility in mineral oil of approximately 7/mg/ml at 32° C. whereas timolol maleate is substantially insoluble in mineral oil. Thus, for example, by impregnating the micropores of microporous polypropylene membrane (Celgard 2400, product of Celanese Corp.) with mineral oil, and measuring flux of timolol or various buffered compositions of timolol maleate, transport across the membrane was observed. Without impregnating the micropores with mineral oil, there would be no selective transport of timolol across the membrane. Illustrative successful transport across a membrane prepared in the foregoing manner are the following representative observed flux, $J_{obs}$ (Table II).

TABLE II

| pH | Reservoir Drug Concentration (mg/ml) | $J_{obs}$ Observed Flux (mcg/cm$^2$/hr) |
|---|---|---|
| 10.4 | 8 mg/ml timolol (base) | 66.0 |
| 9.2 | 70 mg/ml timolol maleate | 18.1 |
| 7.5 | 116 mg/ml timolol maleate | 10.3 |
| 6.8 | 70 mg/ml timolol maleate | 2.8 |

EXAMPLE III

Several pH controlled reservoir systems were prepared in a similar manner employing non-aqueous or aqueous glycol vehicles and different buffering agents. For this example, sorbitol USP and 70 percent aqueous propylene glycol were employed. The pH was adjusted with either Na$_2$HPO$_4$ or Na$_2$CO$_3$. pH measurements were made on a pH meter with a standard glass electrode and the flux determined in a diffusion cell employing a mineral oil soaked Celgard membrane to separate the buffered reservoir from the receptor phase. The results are seen in Table III.

TABLE III

| Reservoir Vehicle | Apparent pH | Solubility of Timolol Maleate (mg/ml as base) | $J_{obs}$ (mcg/cm$^2$/hr) |
|---|---|---|---|
| Sorbitol USP +Na$_2$HPO$_4$ | 6.9 | 17.2 | 6.7 |
| Sorbitol USP +Na$_2$CO$_3$ | 9.6 | 0.7 | 2.8 |
| 70% Propylene | 7.6 | 124.5 | 7.4 |

TABLE III-continued

| Reservoir Vehicle | Apparent pH | Solubility of Timolol Maleate (mg/ml as base) | $J_{obs}$ (mcg/cm²/hr) |
|---|---|---|---|
| glycol +Na₂CO₃ | | | |

It is noted from above that the choice of the buffering agent is critical as it will affect flux by altering the solubility of the salt in the reservoir phase.

EXAMPLE IV

This example illustrates with sulindac the operation of a pH controlled reservoir when the drug is one with an acidic functional group.

As a first step, a 450 μg/ml solution of sulindac free acid in a 30 percent volume/volume (v/v) solution of ethanol in water was placed in the donor chamber of a side-by-side diffusion cell maintained at 32° C. The donor phase was separated from the receptor phase of 30 percent (v/v) ethanol in pH 7.4 isotonic phosphate buffer by a 1.5 mil (0.0038 cm) polyether based polyurethane membrane.

Both donor and receptor phases were stirred at 1500 RPM and the receptor phase sampled at 30 minute intervals for two hours and hourly then to five hours. Samples were assayed by direct ultraviolet absorbance spectroscopy and drug concentration over time calculated. Thereafter, in a manner similar to that described in Example I, average drug flux was calculated based upon average amount of drug diffused per square centimeters over each time interval. From the readings obtained, the steady state flux, J, in the system was found to be 116.4 mcg/cm²/hr.

All the sulindac in a solution of 30 percent ethanol in water was assumed to be unionized in the donor phase. The concentration in 30 percent ethanol/water is 450 μg/ml. Substituting these figures for J and C, and 0.0038 cm for membrane thickness, h in Equation (1), the product, KD, was calculated to be $9.38 \times 10^{-4}$ cm²/hr.

A series of buffered hydroalcoholic solutions of sulindac then were prepared with reduction in concentration of the diffusing species (the unionized acid) produced by increasing the pH. The solutions contained 30 percent v/v ethanol in water buffered with 1/15 molar monobasic potassium phosphate and dibasic sodium phosphate to achieve specified pH values. The total sulindac concentration (ionized plus unionized) was 450 μg/ml in each solution. SH is employed in the equations to represent unionized sulindac and S⁻ the ionized form. The pH of each solution was measured with a pH meter which had been standardized with aqueous reference standards so that the true hydrogen ion activity, $pa_H^*$, can be estimated as specified in R. G. Bates, *Determination of pH Theory and Practice*, 1st Ed., 1964, John Wiley and Sons, New York, N.Y., p. 223-4, where $pa_H = pH - \delta$, and $\delta$ is ~0.1 pH unit for a 30 percent ethanol-water mixture.

Diffusion rates for unionized sulindac from the buffered solution through the 1.5 mil polyurethane membrane were determined in the manner described for the unbuffered solution.

The theoretical diffusion rate was estimated by estimating sulindac's ionization constant in ethanol-water ($Ka_{SH}$) as $$\frac{Ka_{SH}}{Ka} \simeq \frac{K_{SH}/[S^-]}{K_w/[OH^-]}$$

when pH=pKa in aqueous solution and pH=pKa$_{SH}$ in hydroalcoholic solution, and where $K_a$ is sulindac's ionization constant in water, $Ka_{SH}$ is sulindac's ionization constant in 30 percent ethanol-water, and $K_{SH}$ and $K_w$ are the autoprotolysis constants of 30 percent ethanol-water cosolvent and pure water, respectively. [S⁻] and [OH⁻], the concentrations of the deprotonated forms of solvents, were assumed to be negligibly small and equivalent at pH 4 to 5, thus the equation becomes $$Ka_{SH}/Ka \simeq K_{SH}/K_w$$

$K_{SH}$ was estimated to be 14.5 from reported literature values for ethanol-water mixtures (Laitinen et al, *Chemical Analysis*, 2nd Ed., 1975, McGraw-Hill, Inc. New York, N.Y. p. 84). From the reported pKa of 4.7 for sulindac in water at 25° C. and the known pKa of water at 25° C. of 14, pKa$_{SH}$ was calculated to be 5.2. The theoretical concentration of the unionized diffusing species was then calculated and the pH values corrected by the factor δ. No corrections were made for temperature. The theoretical values then were determined by calculating the ionized acid concentration from equation (3) and the expected flux from equation (1) employing the previously determined value for KD. The observed and theoretical values are as follows:

TABLE IV

| pH Observed | pH Calculated (pH Observed - δ) | Flux Observed $J_{obs}$ (μg/cm² hr.) | Theoretical Flux $J_{Theory}$ (μg/cm²hr.) |
|---|---|---|---|
| 4.97 | 4.87 | 80.2 | 79.1 |
| 5.50 | 5.40 | 45.1 | 44.9 |
| 6.44 | 6.34 | 12.0 | 7.8 |

What is claimed is:

1. A method for controlled release of a weakly acidic or basic substantially unionized drug in a transdermal delivery system which comprises providing the drug in a pH controlled reservoir, said reservoir comprising ionized and unionized forms of the drug in a buffered solution and allowing the drug to pass from the drug reservoir through a membrane selectively permeable to the unionized form of the drug and substantially impermeable to the ionized form of the drug.

2. A method of administering timolol transdermally as a free base under controlled conditions comprising providing timolol in a pH rate controlling reservoir, said reservoir comprising ionized and unionized forms of timolol, a buffering agent and a vehicle in which both forms of timolol are soluble, and allowing timolol to pass from the reservoir to the dermal surface by positive pH control through a membrane selectively permeable to but not rate controlling for the unionized free base form of timolol and impermeable to the ionized salt form of timolol.

3. A transdermal delivery system suitable for administering a weakly acidic or basic drug which comprises
 (a) a substantially impermeable backing member,
 (b) a drug reservoir comprising the drug in both ionized and unionized forms, a hydroxylated solvent and a buffering agent, and (c) a membrane selectively permeable to but not rate controlling for the unionized form of the drug and substantially impermeable to the ionized form of the drug and the buffer salts.

4. A system according to claim 3 wherein the drug is timolol.

5. A transdermal delivery system for delivery of acidic or basic drugs comprising
   (a) a backing member substantially impermeable to the drug,
   (b) a drug reservoir adjacent to the backing member comprising both ionized and unionized forms of the drug, and a buffering agent dispersed in a carrier, said carrier being permeable to the drug, and
   (c) a membrane selectively permeable to but not rate controlling for the unionized form of the drug and substantially impermeable to the ionized form; wherein the concentration of the drug in the unionized form, C, and the membrane thickness, h, is related in a manner to provide a flux, J, in accordance with the equation $$J = (K.D.C.)/h$$

wherein K is the partition coefficient between the drug reservoir and the membrane and D is the drug diffusion coefficient in the membrane.

6. A transdermal delivery system for delivery of acidic or basic drugs comprising
   (a) a substantially impermeable backing member,
   (b) a drug reservoir adjacent to the backing member comprising both ionized and unionized forms of the drug in a pH controlled buffer system of a buffering agent and a vehicle in which both forms of the drug are soluble, said system providing a rate controlling pH environment by controlling the concentration of the unionized basic or acidic form of the drug, and
   (c) a membrane permeable to the passage of but not rate controlling for the drug in the unionized form and substantially impermeable to passage of the drug in the ionized form.

7. An improved transdermal bandage for delivery of basic or acidic drugs comprising
   (a) an impermeable backing member
   (b) a drug reservoir comprising a drug in both ionized and unionized forms, a buffering agent and a reservoir vehicle, and
   (c) a membrane selectively permeable to but not rate controlling for the unionized form of the drug.

8. A bandage according to claim 7 which has, in addition, an adhesive coating along the surface of the selectively permeable membrane for attachment to the skin or mucosa.

9. A system according to claim 3 wherein the drug is sulindac.

* * * * *

UNITED STATES PATENT AND TRADEMARK OFFICE
CERTIFICATE OF CORRECTION

PATENT NO.  : 4,756,710
DATED       : July 12, 1988
INVENTOR(S) : JOSEPH V. BONDI, E. LOPER and EDWARD M. COHEN It is certified that error appears in the above-identified patent and that said Letters Patent is hereby corrected as shown below:

Cover page: under "Other Publications" correct "Merk" to --Merck--

Signed and Sealed this

Eighteenth Day of April, 1989

*Attest:*

DONALD J. QUIGG

*Attesting Officer*    *Commissioner of Patents and Trademarks*